Figure 1:
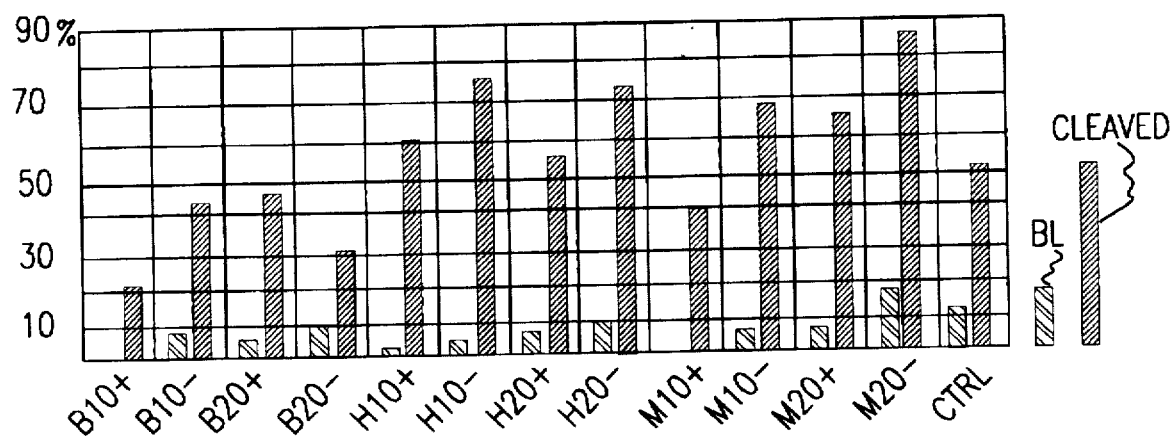

United States Patent [19]

Simmons et al.

[11] Patent Number: 5,716,847
[45] Date of Patent: Feb. 10, 1998

[54] BUFFERED EMBRYO SOLUTIONS

[75] Inventors: Maxine Helen Simmons, 113 Amreins Road, Taupaki, Auckland 1009; Rosemary Katherine Cameron Sharpin, 74 Arney Road, Remuera, Auckland; Jeremy Gilbert Elliot Thompson, Hamilton, all of New Zealand

[73] Assignees: Maxine Helen Simmons; Rosemary Katherine Cameron Sharpin, both of Auckland, New Zealand

[21] Appl. No.: 539,679

[22] Filed: Oct. 5, 1995

[30] Foreign Application Priority Data

Oct. 7, 1994 [NZ] New Zealand .................. 264638

[51] Int. Cl.$^6$ ............................................. C12N 5/02
[52] U.S. Cl. ............................................. 435/404
[58] Field of Search ......................... 435/240.2, 404

[56] References Cited

PUBLICATIONS

Miyoshi et al. Development of rat one-cell embryos in a chemically defined medium: effects of glucose, phosphate and osmolarity. J. Reproduction and Fertility vol. 100 pp. 21–26, 1994.

Pope et al. In vitro development of mouse wmbryos after cryopreservation in phosphate or Hepes buffered media in two different size straws. Theriogenology vol. 41 1613–1619, 1994.

Sigma Cell Culture 1994 Catalogue pp. 15, 28, 244, and 259, 1994.

Carnevale et al. Comparison of Ham's F10 with CO2 or Hepes buffer for storage of equine embryos at 5C for 24 H. J. Animal Science vol. 65 1775–1781, 1987.

*Primary Examiner*—James Ketter
*Assistant Examiner*—John S. Brusca
*Attorney, Agent, or Firm*—Young & Thompson

[57] ABSTRACT

Aqueous buffered physiological solutions suitable for use with embryos are disclosed based on a selection of zwitterionic buffers, allowing improved embryo solutions to be produced, giving a greater holding time than conventional phosphate buffers. An embryo flushing solution and an embryo holding solution based on these bufers are described. A preferred buffered embryo holding solution contains the following ingredients: NACl, MOPS (3-[N-morpholino] propane sulfonic acid]), KCl, $CaCl_2.2H_2O$, $MgCl_2.6H_2O$, $NaHCO_3$, Kanamycin Sulphate, Glucose, Bovine Albumin, Na Lactate, NaOH, and tissue culture grade water.

10 Claims, 1 Drawing Sheet

BUFFERED EMBRYO SOLUTIONS

TECHNICAL FIELD OF THE INVENTION

This invention relates to buffered physiological solutions, and has particular application to embryo holding solutions and embryo transfer solutions.

BACKGROUND

Conventional embryo holding solutions rely on phosphate buffers, and typically have high glucose content. We have found that phosphate buffers do not allow for long holding times for embryos, and there is thus the need for an improved buffered embryo solution.

OBJECT

It is an object of this invention to provide an improved buffered embryo solution or one which will at least provide the public with a useful choice.

STATEMENT OF THE INVENTION

In one aspect, the invention provides an aqueous buffered physiological solution suitable for use with embryos, said solution containing one or more carbon sources, one or more biologically compatible salts, and a buffer, wherein the solution has a pH in the range of 6.8 to 7.8 and the buffer is chosen from the class of zwitterionic buffers.

More preferably the pH is in the range of 7.3 to 7.4.

Preferably the carbon source is chosen from the class of sugars, and more preferably it is glucose.

Preferably the zwitterionic buffer is chosen from the group comprising 3-[N-morpholino]propane sulfonic acid, N-[2-Hydroxyethyl]piperazine-N'-[2-ethanesulfonic acid], N,N-bis[2-Hydroxyethyl]-2-aminoethanesulfonic acid, (1,3-bis[tris(Hydroxymethyl)methylamino]propane) (N,N-bis[2-Hydroxyethyl]-2-aminoethanesulfonic acid; 2-[bis(2-Hydroxyethyl)amino]ethanesulfonic acid) (N-tris[Hydroxymethyl]methyl-2-aminoethane-sulfonic acid; 2-([2-Hydroxy-1,1-bis(hydroxymethyl)ethyl]amino)ethanesulfonic acid. 3-[N,N-bis(2-Hydroxyethyl)methylamino]-2-hydroxy-propanesulfonic acid) (3-[N-tris(Hydroxymethyl)methylamino]-2-hydroxypropanesulfonic acid) (tris[Hydroxymethyl]aminomethane),(2-amino-2-(hydroxymethyl)-1,3-propanediol) (N-[2-Hydroxyethyl]piperazine-N'-[2-hydroxy-propanesulfonic acid]) (Piperazine-N,N'-bis[2-hydroxypropanesulfonic acid]) (N-[2-Hydroxyethyl]piperazine-N'-[3-propane-sulfonic acid]; and Triethanolamine, (2,2'2"-Nitrilotriethanol)

In the case of an embryo holding solution it is preferred that the solution also contains an effective amount of albumin. However in the case of an embryo flushing solution based on these buffers then the albumin is omited.

Preferably the buffered solution contains sodium chloride in the range of 1.0–10.0 g/L.

Preferably the solution also contains potassium chloride in the range of 0.1–1.0 g/L.

Preferably the solution contains sodium bi-carbonate in the range of 0.1–1.0 g/L.

Preferably the solution contains glucose in the range of 0.01–1.0 g/L.

Preferably the solution contains albumin in the form of bovine albumin in the range of 0.01–10.00 g/L.

Preferably the solution contains one or more of the following ingredients: sodium lactate in the range of 0.1–5.0 g/L, kanamycin sulphate in the range of 0.01–0.1 g/L, magnesium chloride in the range of 0.05–0.2 g/L, and calcium chloride in the range 0.1–0.2 g/L.

Preferably the water is tripled distilled water and is of a purity sufficient for embryo holding solutions, typically referred to as "tissue culture grade water".

More preferably the zwitterionic buffer is chosen from the group comprising 3-[N-morpholino]propane sulfonic acid (called "MOPS"); N-[2-Hydroxyethyl]piperazine-N'-[2-ethanesulfonic acid](called "HEPES"); and N,N-bis[2-Hydroxyethyl]-2-aminoethanesulfonic acid (called "PES").

Most preferably the buffered solution contains 3-[N-morpholino]propane sulfonic acid, in the range of 0.1–10.0 g/L.

Although these three zwitterionic buffers are the preferred buffers, being most suitable over the pH range required for "embryo comfort", other zwitterionic buffers may be used, and it is noted that the following zwitterionic buffers can also be adapted for use in the preferred pH range of about 7.3–7.4:

BIS-TRIS PROPANE (1,3-bis[tris(Hydroxymethyl)methylamino]propane)

BES (N,N-bis[2-Hydroxyethyl]-2-aminoethanesulfonic acid; 2-[bis(2-Hydroxyethyl)amino]ethanesulfonic acid)

TES (N-tris[Hydroxymethyl]methyl-2-aminoethane-sulfonic acid; 2-([2-Hydroxy-1,1-bis(hydroxymethyl)ethyl]amino)ethanesulfonic acid.

DIPSO 3-[N,N-bis(2-Hydroxyethyl)methylamino]-2-hydroxy-propanesulfonic acid)

TAPSO (3-[N-tris(Hydroxymethyl)methylamino]-2-hydroxypropanesulfonic acid)

TRIZMA (tris[Hydroxymethyl]aminomethane),(2-amino-2-(hydroxymethyl)-1,3-propanediol)

HEPPSO (N-[2-Hydroxyethyl]piperazine-N'-[2-hydroxy-propanesulfonic acid])

POPSO (Piperazine-N,N'-bis[2-hydroxypropanesulfonic acid])

EPPS (N[2-Hydroxyethyl]piperazine-N'-[3-propane-sulfonic acid]; HEPPS)

TEA Triethanolamine, (2,2'2"-Nitrilotriethanol)

These and other aspects of this invention, which should be considered in all its novel aspects, will become apparent from the following description, which is given by way of reference to the following examples: In addition, the invention is illustrated by means of the associated FIGURE:

FIG. 1: a graph showing the capacity of various buffers to support development of IVP-produced cattle embryos.

EXAMPLE 1

A first preferred embryo holding solution is made up as follows:

| Component | grams/L | Concentration mM |
| --- | --- | --- |
| NaCl | 7.0 g/L | 120 |
| MOPS | 4.182 g/L | 20.0 |
| KCl | 0.4 g/L | 5.4 |
| CaCl$_2$.2H$_2$O | 0.1325 g/L | 0.9 |
| MgCl$_2$.6H$_2$O | 0.1 g/L | 0.5 |
| NaHCO$_3$ | 0.420 g/L | 5.0 |
| Kanamycin Sulphate | 0.025 g/L | |
| Glucose | 0.18 g/L | 1.0 |
| Bovine Albumin | 4.0 g/L | 10.0 |

-continued

| Component | grams/L | Concentration mM |
|---|---|---|
| Na Lactate | 0.84 g/L | |
| NaOH— | adjust pH to 7.3–7.4 | |
| Tissue culture grade water. | | |

The osmolarity of the holding solution is between 260–320 mOSm.

EXAMPLE 2

A preferred embryo flushing media (EFM) is made as follows:

| Component | grams/L |
|---|---|
| NaCl | 7.0 g/L |
| MOPS free acid | 1.78 g/L |
| KCl | 0.4 g/L |
| $CaCl_2.2H_2O$ | 0.13 g/L |
| $MgCl_2.6H_2O$ | 0.1 g/L |
| $NaHCO_3$ | 0.17 g/L |
| Kanamycin Sulphate | 0.03 g/L |
| Glucose | 0.18 g/L |
| Na Lactate (60% syrup) | 1.83 g/L |

By adding 4.0 g/L of gamma-irradiated albumen, we can produce as Embryo Holding Media (EHM (see later)).

By adding the following to one liter of EHM, we produce the variants listed:

| component | variant |
|---|---|
| 100 mL glycerol | 10% v/v glycerol in EHM |
| 342 g sucrose | 34.2% v/v sucrose in EHM |
| 103 g sucrose | 10.3% v/v sucrose in EHM |
| 103 g sucrose + 30 mL glycerol | 10.3% v/v sucrose and 3% v/v glycerol in EHM |
| 103 g sucrose + 60 mL glycerol | 10.3% v/v sucrose and 6% v/v glycerol in EHM |
| 83.58 mL ethylene glycol | 1.5 M ethylene glycol in EHM |
| 83.58 mL ethylene glycol + 68.4 g sucrose | 1.5 M ethylene glycol and 0.2 M sucrose in EHM |

VARIATIONS

Instead of MOPS, other zwitterionic buffers could be used, and in particular HEPES (N-[2-Hydroxyethyl] piperazine-N'-[2-ethanesulfonic acid]) or PES (N,N-bis[2-Hydroxyethyl]-2-aminoethanesulfonic acid). The zwitterionic buffers can be used in the range between 0.1–10.0 g/L. It will be appreciated that the preferred solution in example 1 has a reduced glucose content compared to conventional phosphate buffers, and that the various components can be varied, to make a range of embryo solutions depending upon the holding time required, or other user requirements. For example the ingredients contained in example 1 could be varied as follows:

| Component | Range |
|---|---|
| NaCl | 5.0–10.0 g/L |
| MOPS | 0.1–10.0 g/L |
| KCl | 0.1–1.0 g/L |
| $CaCl_2.2H_2O$ | 0.1–0.2 g/L |
| $MgCl_2.6H_2O$ | 0.05–0.2 g/L |
| $NaHCO_3$ | 0.1–1.0 g/L |
| Kanamycin Sulphate | 0.01–0.1 g/L |
| Glucose | 0.1–1.0 g/L |
| Bovine Albumin | 0.1–10.0 g/L |
| Na Lactate | 0.1–2.0 g/L |
| NaOH— | adjust pH to 7.3–7.4 |
| Tissue culture grade water. | |

TRIALS

1. CONSTANCY OF pH

This table shows the extremes of the ranges of pH values attained after holding various buffers at various temperatures for 15 days. The observed variations are considered to be acceptable.

| Temp-deg C. | 4 min | 4 max | 15 min | 15 max | 25 min | 25 max | 39 min | 39 max |
|---|---|---|---|---|---|---|---|---|
| pH range: | | | | | | | | |
| BES-10 mM | 7.33 | 7.45 | 7.43 | 7.45 | 7.35 | 7.40 | 7.27 | 7.30 |
| BES-20 mM | 7.36 | 7.45 | 7.41 | 7.45 | 7.33 | 7.36 | 7.24 | 7.29 |
| BES-30 mM | 7.35 | 7.45 | 7.41 | 7.44 | 7.33 | 7.35 | 7.23 | 7.28 |
| HEPES-10 mM | 7.55 | 7.58 | 7.57 | 7.59 | 7.52 | 7.54 | 7.44 | 7.48 |
| HEPES-20 mM | 7.53 | 7.60 | 7.56 | 7.60 | 7.51 | 7.53 | 7.45 | 7.47 |
| HEPES-30 mM | 7.53 | 7.60 | 7.56 | 7.59 | 7.50 | 7.53 | 7.44 | 7.47 |
| MOPS-10 mM | 7.35 | 7.42 | 7.39 | 7.42 | 7.33 | 7.37 | 7.23 | 7.29 |
| MOPS-20 mM | 7.33 | 7.41 | 7.37 | 7.41 | 7.31 | 7.34 | 7.22 | 7.27 |
| MOPS-30 mM | 7.33 | 7.40 | 7.37 | 7.39 | 7.30 | 7.33 | 7.22 | 7.26 |

2. METABOLIC MEASUREMENTS OF EMBRYOS.

We have compared a buffer made up according to the most preferred form of the invention (EHM) incorporating redefined proportions of substrates and a zwitterionic buffer, against OCM (Ovum Culture Media) both being supplemented with 4 mg/ml of bovine serum albumen.

Day 7 bovine in vitro-produced (IVP) embryos were derived using techniques described by Pugh et al (Proc NZ Anim Prod 1994; 52: 351–352). Grade 1 and 2 blastocysts were removed from culture, washed, and individually placed in 100 µl OCM or EHM in 0.5 ml Eppendorf tubes and maintained at 25 deg C. After 24 or 48 hours storage, embryos were removed and assessed; either for continued development to hatching in vitro (N=107) by incubation in SOFaaBSA plus 5% FCS at 39 deg C., or for production of $^{14}CO_2$ from [2-$^{14}C$]-pyruvate and incubated at 39 deg C. for 3 hours. Radioactivity of the NaOH trap was measured using a liquid scintillation counter.

Analysis of pyruvate utilization by least-squares analysis revealed a significant (P<0.001) increase in $^{14}CO_2$ production from embryos stored in EHM compared to OCM. Chi-square analysis of redevelopment to hatching also showed a significant (P<0.001) improvement in embryonic viability after storage in EHM at 25 deg C. Both $^{14}CO_2$ production and development after storage significantly (P<0.001) decreased from 24 to 48 h. The invention therefore appears to provide a better embryo storage medium.

3. CAPACITY TO SUPPORT OOCYTE DEVELOPMENT

A 3×2×1 (+1) experimental design compared the three zwitterionic buffers BES, HEPES, and MOPS, under two buffer concentrations (10 mM vs 20 mM), and under two gas atmospheres (5% $CO_2$, 7&!% $O_2$, 88% $N_2$ vs 7% $O_2$, 93% $N_2$. A control group in bicarbonate buffered medium in 5% $CO_2$, 7% $O_2$, 88% $N_2$ was included. Embryo toxicity during development was assessed using in vitro-produced cattle embryos. It was concluded that (a) 10 mM concentration is less effective than 20 mM, zwitterionic buffers are better without $CO_2$ enrichment, and MOPS was less toxic in terms of cleavage than either BES or HEPES. In fact, under MOPS, 20 mM, no $CO_2$, 87% of embryos reached the cleavage stage, whereas only 20% of BES, 10 mM, with $CO_2$, reached cleavage. Results are illustrated as FIG. 1. In FIG. 1, the vertical scale shows the percentage of embryos that reach the cleavage stage. For each label along the horisontal axis, B. H. or M represents BES, HEPES, or MOPS, 10 or 20 indicates concentration, and + or − indicates presence or absence of carbon dioxide. It can be seen that the highest bar lies over the M20− label, corresponding to MOPS, 20 mM, and no carbon dioxide.

4. ADDITIONAL COMPONENTS:

We tested addition of ethylene diamine tetra acetic acid (EDTA), glycine, and betaine. We measured embryo viability using the [2-$^{14}$C]-pyruvate utilisation assay as described above, and observed little if any significant improvement.

5. DEVELOPMENT AFTER FREEZING—BOVINE EMBRYOS

EHM is comparable to OCM when used as a base solution in embryo freezing and thawing procedures.

| Freezing media | Total embryos | Development |
| --- | --- | --- |
| EHM | 84 | 42.9% |
| OCM | 72 | 41.7% |

6. BOVINE EMBRYO DEVELOPMENT AFTER EXPOSURE TO OLD SOLUTIONS

The next experiment tested degradation in samples of storage media which had been set aside in storage for various periods. The embryos were placed in the media under test for 24 hours at 25 deg C. Evidently, storage of the zwitterionic media does not adversely affect its performance, as compared to OCM.

| Storage media- | Total embryos | Development |
| --- | --- | --- |
| 85 days old | | |
| EHM | 37 | 37.8% |
| OCM | 35 | 8.6% |
| 180 days old | | |
| EHM | 12 | 66.7% |
| OCM | 7 | 57.1% |
| 215 days old | | |
| EHM | 21 | 85.7% |
| OCM | 20 | 75% |

ADVANTAGES

It has been found that the buffered embryo solutions of this invention have increased holding times compared to phosphate buffers, and provide for more viable embryos than with conventional phosphate buffers.

Finally it will be appreciated that various other alterations and modifications may be made to the foregoing without departing from the scope of this invention, as set forth in the claims.

We claim:

1. An aqueous buffered physiological solution suitable for use with embryos, said solution containing at least one carbon source, at least one biologically compatible salt, and a buffer, wherein the solution is free from sufficient phosphate to have a buffering effect and has a pH in the range of 6.8 to 7.8 and the buffer is a zwitterionic buffer selected from the group consisting of:

3-[N-morpholino] propane sulfonic acid; N,N-bis[2-Hydroxyethyl]-2-aminoethanesulfonic acid; (1,3-bis [tris(Hydroxymethyl)methylamino]propane); (N,N-bis [2-Hydroxyethyl]-2-aminoethanesulfonic acid; 2-[bis (2-Hydroxyethyl)amino]ethanesulfonic acid); (N-tris [Hydroxymethyl]methyl-2-aminoethane-sulfonic acid; 2-([2-Hydroxy-1,1-bis(hydroxymethyl)ethyl]amino) ethanesulfonic acid; 3-[N,N-bis(2-Hydroxyethyl) methylamino]-2-hydroxypropanesulfonic acid); (3-[N-tris (Hydroxymethyl)methylamino]-2-hydroxypropanesulfonic acid); (tris[Hydroxymethyl] aminomethane), (2-amino-2-(hydroxymethyl)-1,3-propanediol); (N-[2-Hydroxyethyl]piperazine-N'-[2-hydroxypropanesulfonic acid]); (Piperazine-N,N'-bis [2-hydroxypropanesulfonic acid]); (N[2-Hydroxyethyl]piperazine-N'-[3-propane-sulfonic acid] ); Triethanolamine, (2,2'2"-Nitrilotriethanol); and mixtures thereof.

2. A buffered solution as claimed in claim 1, wherein said solution also contains albumin, and the at least one carbon source is glucose.

3. A buffered solution as claimed in claim 1, wherein the buffered solution contains sodium chloride in the range of 1.0–10.0 g/L.

4. A buffered solution as claimed in claim 1, wherein the buffered solution contains 3-[N-morpholino] propane sulfonic acid in the range of 0.1–10.0 g/L.

5. A buffered solution as claimed in claim 1, wherein the solution also contains potassium chloride in the range of 0.1–1.0 g/L.

6. A buffered solution as claimed in claim 1, wherein the solution contains sodium bicarbonate in the range of 0.05–1.0 g/L.

7. A buffered solution as claimed in claim 1, wherein the solution contains glucose in the range of 0.05–1.0 g/L.

8. A buffered solution as claimed in claim 1, wherein the solution contains albumin in the form of bovine albumin in the range of 0.01–10.0 g/L.

9. A buffered solution as claimed in claim 1, wherein the solution contains at least one of the following ingredients:
sodium lactate in the range of 0.1–5.0 g/L,
kanamycin sulphate in the range of 0.01–0.1 g/L,
magnesium chloride in the range of 0.05–0.2 g/L, or
calcium chloride in the range of 0.1–0.2 g/L.

10. An aqueous buffered physiological solution suitable for use with embryos, said solution containing at least one carbon source, at least one biologically compatible salt, and a buffer, wherein the solution has a pH in the range of 6.8 to 7.8 and the buffer is a non-phosphate buffer and is a zwitterionic buffer selected from the group consisting of:

3-[N-morpholino] propane sulfonic acid; N,N-bis [2-Hydroxyethyl]-2-aminoethanesulfonic acid; (1,3-bis

[tris(Hydroxymethyl)methylamino]propane); (N,N-bis[2-Hydroxyethyl]-2-aminoethanesulfonic acid; 2-[bis(2-Hydroxyethyl)amino]ethanesulfonic acid); (N-tris[Hydroxymethyl]methyl-2-aminoethane-sulfonic acid; 2-([2-Hydroxy-1,1-bis(hydroxymethyl)ethyl]amino) ethanesulfonic acid; 3-[N,N-bis(2-Hydroxyethyl)methylamino]-2-hydroxypropanesulfonic acid); (3-[N-tris(Hydroxymethyl)methylamino]-2-hydroxypropanesulfonic acid); (tris[Hydroxymethyl]aminomethane), (2-amino-2-(hydroxymethyl)-1,3-propanediol); (N-[2-Hydroxyethyl]piperazine-N'-[2-hydroxypropanesulfonic acid]); (Piperazine-N,N'-bis[2-hydroxypropanesulfonic acid]); (N[2-Hydroxyethyl]piperazine-N'-[3-propane-sulfonic acid]); Triethanolamine, (2,2'2"-Nitrilotriethanol); and mixtures thereof.

* * * * *